(12) United States Patent
Yamaguchi

(10) Patent No.: US 8,735,806 B2
(45) Date of Patent: May 27, 2014

(54) MASS-ANALYZING METHOD AND MASS SPECTROMETER

(75) Inventor: Shinichi Yamaguchi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 27 days.

(21) Appl. No.: 12/444,811

(22) PCT Filed: Nov. 15, 2006

(86) PCT No.: PCT/JP2006/322740
§ 371 (c)(1),
(2), (4) Date: Apr. 8, 2009

(87) PCT Pub. No.: WO2008/059567
PCT Pub. Date: May 22, 2008

(65) Prior Publication Data
US 2010/0044562 A1    Feb. 25, 2010

(51) Int. Cl.
*H01J 49/26* (2006.01)
*H01J 49/00* (2006.01)

(52) U.S. Cl.
CPC .......... *H01J 49/0036* (2013.01); *H01J 49/004* (2013.01)
USPC ...................................... 250/282

(58) Field of Classification Search
USPC .......................... 250/282; 702/23
See application file for complete search history.

(56) References Cited

U.S. PATENT DOCUMENTS

| | | | | |
|---|---|---|---|---|
| 5,538,897 A | * | 7/1996 | Yates et al. ................ | 436/89 |
| 6,582,965 B1 | * | 6/2003 | Townsend et al. .......... | 436/89 |
| 6,745,134 B2 | * | 6/2004 | Kobayashi et al. .......... | 702/27 |
| 6,907,352 B2 | * | 6/2005 | Yoshinari et al. ........... | 702/23 |
| 6,957,159 B2 | * | 10/2005 | Kobayashi et al. ......... | 702/81 |
| 7,544,931 B2 | * | 6/2009 | Yamaguchi et al. ......... | 250/282 |

(Continued)

FOREIGN PATENT DOCUMENTS

| | | |
|---|---|---|
| EP | 1 376 651 A2 | 1/2004 |
| EP | 1 429 145 A1 | 6/2004 |

(Continued)

OTHER PUBLICATIONS

Japanese Office Action dated Jun. 7, 2011, issued in corresponding Japanese Patent Application No. 2008-544030.

*Primary Examiner* — Jack Berman
*Assistant Examiner* — Eliza Osenbaugh-Stewart
(74) *Attorney, Agent, or Firm* — Sughrue Mion, PLLC

(57) ABSTRACT

Based on the mass spectrum obtained by mass-analyzing a sample, the composition of the unknown substance is deduced, and after that, an MS/MS analysis is performed in which the unknown substance is set to be a precursor ion. Then, based on the peaks appearing on the MS/MS spectrum, the actually measured mass of each product ion is obtained (S1 through S4). On the other hand, the compositions of the product ion generated by the dissociation of the unknown substance are obtained by the combination, i.e. the condition, of the kind of the constituent element and the number of each element of the unknown substance's deduced component. Then, it is checked whether or not the theoretical mass in consistency with the actually measured mass of the product ion exists (S5). In the case where one which is consistent with a theoretical mass is not existent, it is possible to determine that the original deduction of the known substance's composition has been incorrect. Therefore, this result is given to the composition deduction as feedback to refine the candidates for the unknown substance's composition (S6).

4 Claims, 3 Drawing Sheets

(56) References Cited

U.S. PATENT DOCUMENTS

| | | |
|---|---|---|
| 7,763,846 B2* | 7/2010 | Yamaguchi et al. .......... 250/281 |
| 7,781,729 B2* | 8/2010 | Wang et al. ................... 250/282 |
| 8,026,476 B2* | 9/2011 | Yamaguchi ................... 250/282 |
| 2004/0180446 A1* | 9/2004 | Thompson et al. ............. 436/86 |
| 2005/0023454 A1* | 2/2005 | Bateman et al. ............. 250/288 |
| 2005/0063864 A1* | 3/2005 | Sano et al. ................... 422/68.1 |
| 2006/0043281 A1* | 3/2006 | Yoshinari et al. ............. 250/282 |
| 2009/0076737 A1* | 3/2009 | Wang et al. .................... 702/23 |

FOREIGN PATENT DOCUMENTS

| | | |
|---|---|---|
| EP | 1 447 833 A2 | 8/2004 |
| JP | 08-124519 A | 5/1996 |
| JP | 09-510780 A | 10/1997 |
| JP | 2004-028782 A | 1/2004 |
| JP | 2004-191077 A | 7/2004 |
| JP | 2004-245699 A | 9/2004 |
| WO | 95/25281 A1 | 9/1995 |

* cited by examiner

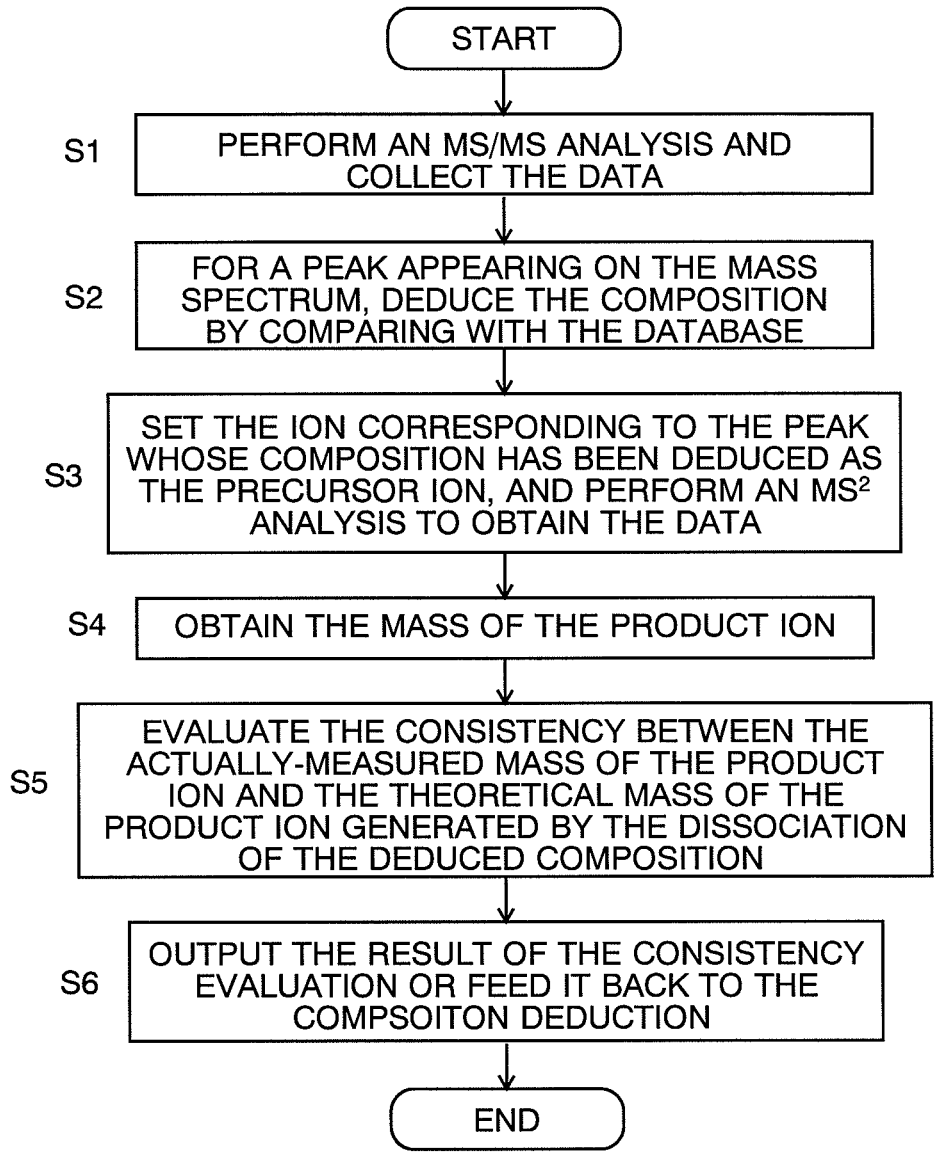

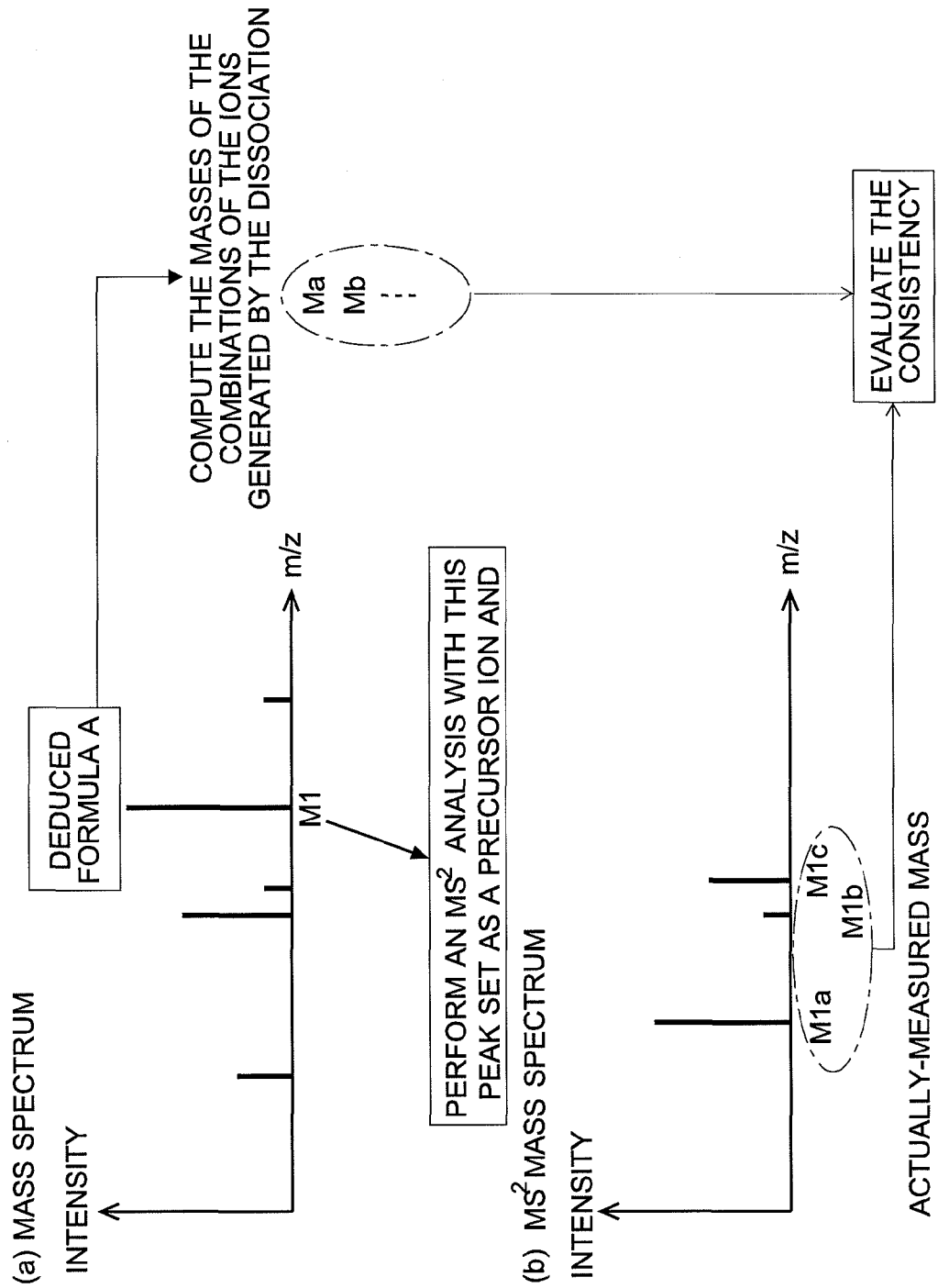

MASS-ANALYZING METHOD AND MASS SPECTROMETER

TECHNICAL FIELD

The present invention relates to a mass-analyzing method for deducing the composition of an unknown substance using an MS$^n$ mass spectrometer capable of analyzing a product ion or ions generated by dissociating an ion to be analyzed. The present invention also relates to a mass spectrometer for performing the mass-analyzing method.

BACKGROUND ART

Mass spectrometers are an apparatus for ionizing a variety of substances contained in a sample and separating the ions in every mass (specifically, the mass-to-charge ratio m/z) to detect them. With a mass spectrometer, the mass of each ion species can be accurately obtained. In identifying the substance contained in the sample, a database may be previously created in which the masses of a variety of substances whose compositions and structures are known are registered. Accordingly, a substance can be identified by comparing the masses of the peaks appearing on the mass spectrum obtained by a mass analysis and the database. Even for a substance which is not registered in the database, if the kinds of elements and the numbers of atoms of these elements constituting the substance are known to some extent, the composition of the unknown substance can be deduced by determining the consistency between the mass of the unknown substance to be identified and the mass obtained by combining a variety of elements.

However, even in the case where a certain unknown substance is identified by a search using a database as previously described for example, the reliability is not necessarily high. That is, a certain level of tolerance is normally set for a mass, in consideration of the mass error of the measurement and mass difference of the isotopes, and the substance is considered to be the correct substance if the consistency is shown within the mass range. However, even a substance whose composition formula is not registered in the database often falls into the mass range. Therefore, although in reality such a substance is the correct substance, in some cases an erroneous identification may be performed.

On the other hand, with an MS/MS (or MS$^n$) mass spectrometer, an ion having a specific mass can be selectively dissociated, and a variety of product ions (or fragment ions) generated by this process are mass analyzed to create an MS$^n$ mass spectrum. In this case, a database is previously created in which the mass and intensity (or fragment pattern) of the product ions are registered for a large number of compositions. Then, the compound can be identified by comparing the mass and intensity of each peak appearing on the MS$^n$ mass spectrum and the database (refer to Patent Document 1 for example).

However, even such an identification method does not always provide a correct result, since a dissociation has more than one mode and it is impractical to register all the fragment patterns in the database.

[Patent Document 1] Japanese Unexamined Patent Application Publication No. H08-124519 (paragraphs [0002] through [0004])

DISCLOSURE OF THE INVENTION

Problems to be Solved by the Invention

The present invention has been devised to solve the aforementioned problems, and the objective thereof is to provide a mass-analyzing method for easily and with high reliability deducing the composition formula of an unknown substance using an MS$^n$ mass spectrometer, and a mass spectrometer for performing the mass-analyzing method.

Means for Solving the Problems

The first aspect of the present invention developed to solve the aforementioned problems provides a mass-analyzing method using a mass spectrometer capable of an MS/MS analysis in which a precursor ion originating from a target substance is dissociated and product ions generated by a dissociation are mass analyzed, for analyzing a composition of the target substance based on data obtained by the mass spectrometer, including:

a) an analysis performing step for setting an unknown substance, whose composition has been deduced by using a result of a mass analysis, to be a precursor ion and performing an MS/MS analysis;

b) a theoretical mass computation step for theoretically obtaining a mass of a fragment which can be generated by a dissociation, based on the composition deduced for the unknown substance; and c) a verification step for verifying a consistency between a mass of one or more product ions appearing on a mass spectrum obtained by the MS/MS analysis in the analysis performing step and the mass obtained in the theoretical mass computation step, and in a case where the consistency is ensured, determining that a reliability of the composition deduced for the unknown substance is high.

The second aspect of the present invention developed to solve the aforementioned problems provides a mass spectrometer, which is an apparatus for realizing the mass-analyzing method according to the first aspect of the invention, capable of an MS/MS analysis in which a precursor ion originating from a target substance is dissociated and product ions generated by a dissociation are mass analyzed, for analyzing a composition of the target substance based on data obtained by a mass analysis, including:

a) an analysis performing section for setting an unknown substance, whose composition has been deduced by using a result of the mass analysis, to be a precursor ion and performing an MS/MS analysis;

b) a theoretical mass computation section for theoretically obtaining a mass of a fragment which can be generated by a dissociation, based on the composition deduced for the unknown substance; and c) a verification section for verifying a consistency between a mass of one or more product ions appearing on a mass spectrum obtained by the MS/MS analysis under a control of the analysis performing section and the mass obtained in the theoretical mass computation section, and in a case where the consistency is ensured, determining that a reliability of the composition deduced for the unknown substance is high.

In the mass-analyzing method and the mass spectrometer according to the present invention, the composition of an unknown substance is deduced, based on the mass spectrum obtained by a mass analysis, for example, by comparing the mass of the unknown substance and a predetermined database or by searching for the combination of the kinds of elements and the numbers of atoms of these elements which correspond to the mass of the unknown substance under previously given conditions of the kinds of constituent elements and the range of the number of atoms of each element. As a matter of course, a plurality of candidates for the compositions may be found in performing such a deduction in some cases. Next, in an analysis performing step, this unknown substance whose composition has been deduced is set to be a precursor ion and an MS/MS analysis is performed in order to obtain an MS/MS mass spectrum on which peaks appear which correspond to a variety of product ions originating from the unknown substance. However, in the case where MS/MS analyses for all peaks appearing on the mass spectrum are sequentially and automatically performed in which each peak is set to be a precursor ion, the analysis performing step is performed before deducing the unknown substance's composition.

On the other hand, in the theoretical mass computation step, the mass of each fragment which can be generated by a dissociation is theoretically obtained based on the composition deduced for the unknown substance. In order to perform this step, under the conditions of the kinds of the constituent elements of the unknown substance's deduced compositions and the number of atoms of each element, the combinations of possible compositions may be obtained and each mass may be computed. In the verification step, the consistency is verified between the mass of a peak (i.e. the peak of a product ion) appearing on the MS/MS mass spectrum, and the theoretical mass of the fragment (i.e. the product ion) obtained based on the unknown substance's deduced composition. In other words, in the case where a theoretical mass corresponding to the mass of the product ion which has been obtained by an actual measurement exists, it can be determined that the reliability of the original deduction of the unknown substance's composition is high. However, in the case where the theoretical mass is not existent, it can be determined that the reliability of the deduction of the unknown substance's composition is low, i.e. the deduction is incorrect. Based on such a verification result, the unknown substance's composition is determined, for example, by redoing the deduction of the unknown substance or by selecting a candidate with high reliability from among a plurality of candidates for the composition which have been lined up in advance.

Effect of the Invention

With the mass-analyzing method and the mass spectrometer according to the present invention, when the unknown substance's composition is deduced based on the result of a mass analysis, an erroneous deduction due to an accidental coincidence or other reasons for example can be eliminated and the reliability of the composition deduction is increased.

BRIEF DESCRIPTION OF THE DRAWINGS

FIG. 2 is a flowchart illustrating an example of the characteristic analytical process operation of the present embodiment.

FIG. 3 is an explanation diagram of the analytical process operation.

EXPLANATION OF NUMERALS

Figure 1:
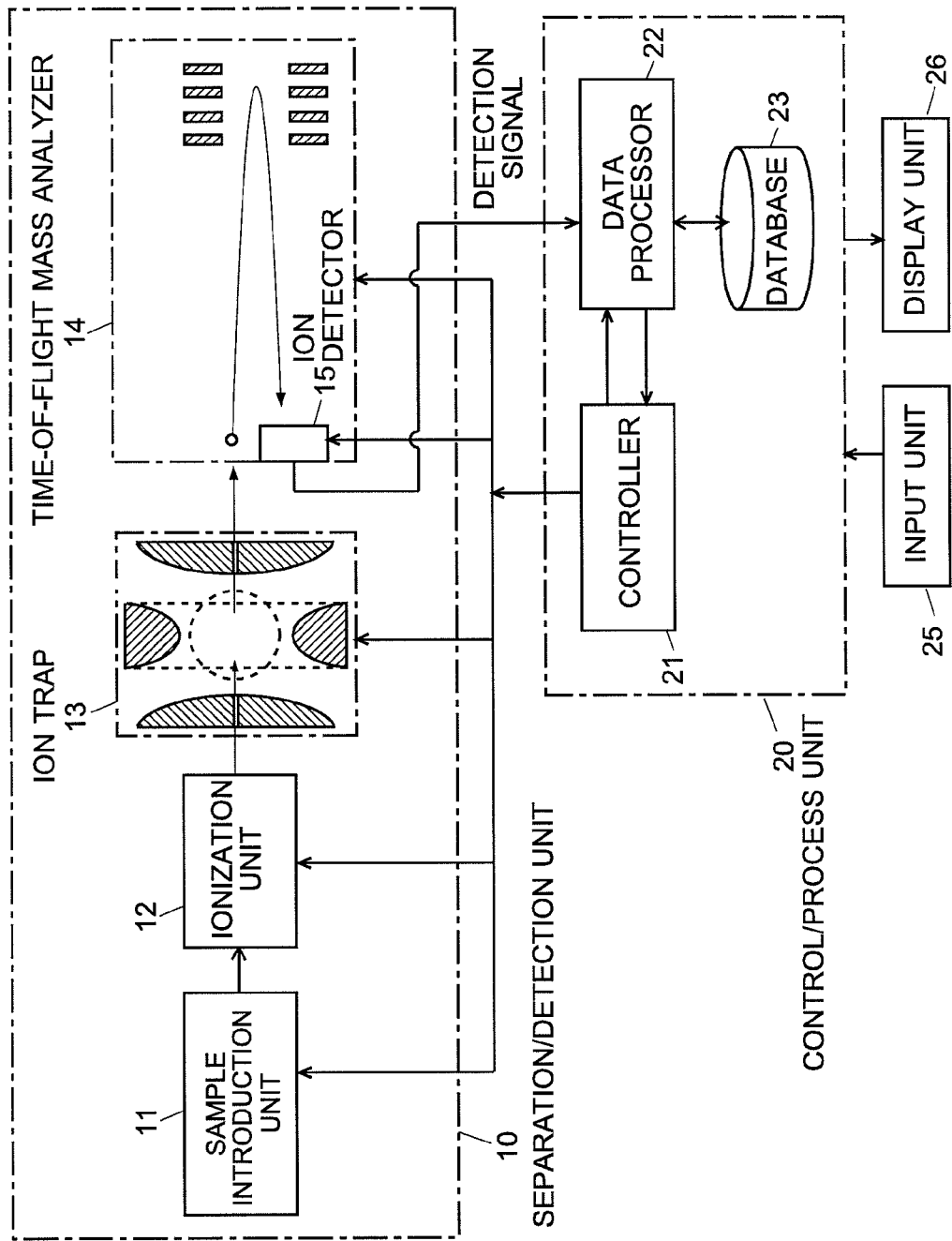
FIG. 1 is an overall configuration diagram of a mass-analyzing system according to an embodiment of the present invention.

10 . . . Separation/Detection Unit
11 . . . Sample Introduction Unit
12 . . . Ionization Unit
13 . . . Three-Dimensional Quadrupole Ion Trap
14 . . . Time-Of-Flight Mass Analyzer
15 . . . Ion Detector
20 . . . Control/Process Unit
21 . . . Controller
22 . . . Data Processor
23 . . . Database
25 . . . Input Unit
26 . . . Display Unit

BEST MODE FOR CARRYING OUT THE INVENTION

Hereinafter, a mass-analyzing data analysis method and an apparatus thereof according to the present invention will be specifically explained with reference to the figures.

FIG. 1 is an overall configuration diagram of a mass-analyzing system which is an embodiment of the present invention. The mass-analyzing system according to the present embodiment is roughly composed of a separation/detection unit 10 and a control/process unit 20. The separation/detection unit 10 includes: an ionization unit 12 for ionizing a sample to be analyzed introduced from a sample introduction unit 11; a three-dimensional quadrupole ion trap 13 capable of temporarily capturing ions and expelling them almost collectively at a predetermined timing; a time-of-flight mass analyzer 14 for temporally separating the introduced ions in accordance with the mass (specifically, the mass-to-charge ratio); and an ion detector 15 for sequentially detecting the separated ions. The ion trap 13 also has a collision-induced dissociation (CID) function in which an ion having a specific mass is selected as a precursor ion and the precursor ion is dissociated by making the precursor ion collide with a CID gas introduced from the outside, and then a variety of product ions generated by the dissociation are stored and almost collectively expelled at a predetermined timing.

The control/process unit 20 includes: a controller 21 for controlling each unit of the separation/detection unit 10; a data processor 22 which performs a predetermined analysis by converting a detection signal from the ion detector 15 into digital data and then processing the data; and a database 23 used in deducing the unknown substance's composition. To the control/process unit 20, an input unit 25 for allowing an analyst to input a variety of settings and commands and a display unit 26 for displaying analysis conditions, analysis results, and other information are connected. Generally, the control/process unit 20 is realized by a commercially available personal computer, and a characteristic operation as will be described later is accomplished by executing dedicated control/process software installed in the computer. In this case, the input unit 25 is a keyboard and a pointing device such as a mouse. As a matter of course, a computer specialized for this operation and not a general-purpose personal computer may be incorporated.

Next, the procedure of a typical analysis using the mass-analyzing system according to the present embodiment will be described with reference to FIGS. 2 and 3. FIG. 2 is a flowchart of the unknown substance's deduction process which is characteristic in the mass-analyzing system according to the present embodiment, and FIG. 3 is an explanation diagram of the operation.

First, a mass analysis (or a scan measurement over a predetermined mass range) in which a dissociation is not performed for the sample to be analyzed is performed to obtain the mass spectrum data (Step S1). In other words, under the control by the controller 21, a sample introduced from the sample introduction unit 11 is ionized in the ionization unit 12 and then introduced into the ion trap 13. In the ion trap 13, the ions are temporarily stored and cooling or other process is performed for example. After that, the ions are collectively expelled to be sent into the time-of-flight mass analyzer 14. While flying in the time-of-flight mass analyzer 14, a variety of ions are separated in accordance with the mass, and ions having a smaller mass reach the ion detector 15 sooner to be detected. The data processor 22 receives the detection signal and converts the flight time into the mass, and then creates a mass spectrum in which a mass is assigned to the horizontal axis and an ion intensity to the vertical axis. At this point, let us suppose that a mass spectrum as illustrated in FIG. 3(a) for example is created as the result of this operation.

In the case of automatically identifying all the substances contained in the sample, the peaks appearing on the mass spectrum are sequentially detected, the mass corresponding to the peak is obtained, and the mass is compared with the data stored in the database 23 in order to search for the substance having a corresponding mass to deduce the composition (Step S2). In consideration of the mass error in a measurement and the slight mass difference in the same element depending on the isotope compositional ratio, a predetermined mass tolerance is defined, and a search is conduced to find any substance which corresponds to the mass tolerance. It should be noted that the composition deduction does not always need to be performed for all the substances contained in the sample but may be performed for a substance corresponding to a specified peak on the mass spectrum.

At this point in time, suppose that a deduced composition A is obtained for an unknown substance having a peak whose mass is Ml in FIG. 3(a). Next, the controller 21 sets the ion of the unknown substance having the mass Ml as the precursor ion and performs an MS/MS analysis for the sample to obtain mass spectrum data (Step S3). Concretely speaking, under the control by the controller 21, the ion trap 13 temporarily captures a variety of ions introduced from the ionization unit 13 and then discharges all the ions other than the precursor ion from the ion trap 13. Subsequently the CID gas is introduced into the ion trap 13 in order to make the precursor ion collide with the CID gas to promote the dissociation, and the product ions generated by the dissociation are captured. After that, the product ions are collectively expelled from the ion trap 13, introduced into the time-of-flight mass analyzer 14, and separated according to each mass to be detected. At this point, let us suppose that the MS/MS mass spectrum as illustrated in FIG. 3(b) for example is created in the data processor 22 as a result of this operation.

Next, the peaks appearing on the MS/MS mass spectrum, i.e. peaks corresponding to the product ions, are detected and each mass is obtained (Step S4). In the example of FIG. 3(b), three masses of M1a, M1b, and M1c are obtained.

On the other hand, the data processor 22 predicts the composition of the product ions and fragments generated when the deduced composition A is dissociated and obtains each mass. At this point in time, in the case where the composition A is $X_L Y_m Z_n$ for example, where each of X, Y, and Z is an appropriate element, it is evident that the product ions and fragments can be expressed within the following range: L atoms of the element X, m atoms of the element Y, and n atoms of the element Z. Therefore, the mass (or theoretical mass) is computed while changing the combination of the kinds of the elements and the combination of the numbers of atoms of these elements. Then, it is verified whether or not the mass Ma, Mb, and other values obtained in such a manner are consistent with the three masses of M1a, M1b, and M1c which have been previously obtained in Step S4 (Step S5).

Practically speaking, in consideration of the accuracy error and other factors of the mass obtained by an actual measurement, the mass range of M1a±ΔM is set for the mass M1a of the product ion obtained by the actual measurement for example, and it is checked whether or not a theoretical mass exists within this mass range. In the case where a corresponding theoretical mass is not existent, it can be determined that the original deduction itself of the unknown substance's composition A is incorrect. On the other hand, in the case where the theoretical masses corresponding to all the product ions obtained by the actual measurement are existent, it can be determined that the reliability of the original deduction of the unknown substance's composition A is high.

Given this factor, the evaluation result of the consistency is displayed on the display unit 26 for example in order to let the operator know the reliability level of the deduction of composition A. This allows the operator to perform an appropriate handling such as redoing the identification operation according to necessity. In the case where a plurality of composition candidates for a single unknown substance are found in Step S2, the estimation result of the consistency may be given as feedback to refine the candidates, and the most reliably deduced composition may be displayed as the final identification result (Step S6).

An explanation is made using a concrete example. At this point in time, suppose that the result of a mass analysis for a certain unknown substance is compared with the database and the deduced composition is $C_6H_{12}O_6$ (mass:180.0634). In a conventional case, this composition is determined to be an unknown substance's composition. On the other hand, in the mass-analyzing method according to the present invention, an MS/MS analysis is performed in which this unknown substance is set to be a precursor ion and an MS/MS mass spectrum is created. Suppose that a peak due to a product ion appears at the mass of 80.0380 in this spectrum. At the same time, supposing that a substance whose composition is $C_6H_{12}O_6$ is dissociated, the composition of the product ion generated by the dissociation should be within the range of the composition of $C_6H_{12}O_6$, in other words, in the maximum condition of six C (carbon), twelve H (hydrogen), and six O (oxygen). The computational result of a composition having a value near the mass of 80.0380 is shown in the following table.

TABLE 1

| # | Mass | Diff. | Formula | DBE |
|---|------|-------|---------|-----|
| 1 | 80.0262 | 11.79 | $C_2H_4O$ | 4.0 |
| 2 | 80.0626 | 24.60 | $C_6H_8$ | 3.0 |

If the measurement error ΔM is set to be 5 mDa, both masses of the two compositions do not correspond to the actually measured mass of the product ion. Therefore, the actually measured mass of the product ion and the theoretical mass of the product ion in the case where the composition is set to be $C_6H_{12}O_6$ are not consistent with each other, and it is concluded that the composition's deduction is incorrect in the first place.

As previously described, with the mass-analyzing method and the apparatus for realizing the same according to the present invention, it is possible to verify whether or not the unknown substance's composition which has been deduced based on the result of a mass analysis is reliable. Therefore, it is possible to prevent an erroneous identification due to an accidental coincidence of the mass for example.

In the aforementioned embodiment, the unknown substance's composition is deduced by comparing the mass of the peak appearing on the mass spectrum obtained by a mass analysis. However, it should be noted that the deduction method of the unknown substance's composition is not limited to this method.

Generally, with the mass spectrometer capable of performing an MS/MS analysis at high speed, an MS/MS analysis can be performed in which a precursor ion set by an operator or other person is set to be a target. In addition, such a mass spectrometer can also perform an MS/MS analysis in which all the peaks or a portion of the peaks appearing on the mass spectrum obtained by the mass analysis are automatically set as a precursor ion. In such a case, it is possible to involve the following procedure: after the automatic completion up to an MS/MS analysis, the composition of the peak appearing on the mass spectrum is deduced, and the MS/MS mass spectrum corresponding to the peak whose composition has been deduced is promptly read out to obtain the mass of the product ion.

It should be noted that the aforementioned embodiment is an example of the present invention, and therefore it is evident that any modification, adjustment or addition properly made within the spirit of the preset invention is also covered by the claims of the present patent application.

The invention claimed is:

1. A mass-analyzing method using a mass spectrometer capable of an MS/MS analysis in which a precursor ion originating from a target substance is dissociated and product ions generated by the dissociation are mass analyzed, for analyzing a composition of the target substance based on data obtained by the mass spectrometer, comprising:
 a) setting an unknown substance, whose composition has been deduced by using a result of a mass analysis, to be a precursor ion, and performing an MS/MS analysis on the precursor ion;
 b) determining kinds of constituent elements and a number of atoms of each constituent element of the unknown substance based on the deduced composition of the unknown substance;
 c) computing a mass of each of possible fragment ions of the precursor ion based on the determined kinds of constituent elements and the number of atoms of each constituent element of the unknown substance by summing individually mass values of the determined kinds of constituent elements in various combinations permitted by the number of atoms of each constituent element, wherein the possible fragment ions are wholly made up of discrete units of the constituent elements;
 d) verifying whether a mass of one or more product ions appearing on a mass spectrum obtained by the MS/MS analysis exists in the computed mass of possible fragment ions; and
 e) determining a reliability of the composition deduced for the unknown substance based on the verification result.

2. The mass-analyzing method according to claim 1, wherein the verified consistency and the determined reliability are shown to an operator.

3. The mass-analyzing method according to claim 1, wherein the verified consistency and the determined reliability are given as feedback to redo the setting the unknown substance and the determining the kinds of the constituent elements and the number of atoms of each of the constituent elements of the unknown substance.

4. The mass-analyzing method according to claim 1, wherein the mass of each of possible fragment ions of the precursor ion is computed within the range of the determined kinds of constituent elements and the number of atoms of each constituent element of the unknown substance, and the mass of each of possible fragment ions of the precursor ion is computed while changing the combination of the kinds of the elements and the numbers of atoms of the elements.

* * * * *